United States Patent [19]

Shepherd et al.

[11] Patent Number: 5,776,188
[45] Date of Patent: Jul. 7, 1998

[54] DIRECT SUTURE ORIFICE FOR MECHANICAL HEART VALVE

[75] Inventors: Terry L. Shepherd, Shoreview; Guy Vanney, Blaine; Kurt D. Krueger, Stacy, all of Minn.

[73] Assignee: St. Jude Medical, Inc., St. Paul, Minn.

[21] Appl. No.: 748,071

[22] Filed: Nov. 12, 1996

Related U.S. Application Data

[63] Continuation of Ser. No. 483,255, Jun. 7, 1995, abandoned.

[51] Int. Cl.⁶ ............................................. A61F 2/24
[52] U.S. Cl. ................................... 623/2; 623/900
[58] Field of Search ...................... 623/2, 3, 66, 900

[56] References Cited

U.S. PATENT DOCUMENTS

| | | |
|---|---|---|
| 3,143,742 | 8/1964 | Cromie . |
| 3,503,079 | 3/1970 | Smith . |
| 3,546,710 | 12/1970 | Shumakov et al. . |
| 3,574,865 | 4/1971 | Hamaker ........................... 128/303 |
| 3,996,623 | 12/1976 | Kaster ................................ 623/2 |
| 4,364,126 | 12/1982 | Rosen et al. ........................ 623/2 |
| 4,612,011 | 9/1986 | Kautzky ............................. 623/2 |
| 5,035,709 | 7/1991 | Wieting et al. ..................... 623/2 |
| 5,071,431 | 12/1991 | Sauter et al. . |
| 5,163,954 | 11/1992 | Curcio et al. . |
| 5,397,346 | 3/1995 | Walker et al. ...................... 623/2 |

FOREIGN PATENT DOCUMENTS

| | | | |
|---|---|---|---|
| 1222264 | 4/1986 | U.S.S.R. ............................. 623/2 |
| WO 91/14408 | 10/1991 | WIPO . |

*Primary Examiner*—John G. Weiss
*Assistant Examiner*—Bruce E. Snow
*Attorney, Agent, or Firm*—Hallie A. Finucane, Esq.

[57] ABSTRACT

A mechanical heart valve for implantation in a heart of a patient includes an orifice body having an outer circumference and defining a lumen for blood flow therethrough. At least one leaflet carried in the lumen of the orifice body is movable between an open position, allowing flow through the lumen, and a closed position blocking flow through the lumen. A flange ring around the outer circumference of the orifice body includes a plurality of suture holes defined therein. The suture holes are adapted for receiving a suture and thereby attaching the heart valve to tissue of the heart.

18 Claims, 9 Drawing Sheets

DIRECT SUTURE ORIFICE FOR MECHANICAL HEART VALVE

This is a file wrapper continuation of application Ser. No. 08/483,255 filed Jun. 7, 1995 now abandoned.

FIELD OF THE INVENTION

The present invention relates to mechanical heart valve prostheses. More specifically, the invention relates to a heart valve orifice which is directly sutured to the heart tissue.

BACKGROUND OF THE INVENTION

Implantable mechanical heart valves are used for replacement of defective valves in hearts of patients. The valves are typically sutured to a tissue annulus that is left when the surgeon removes the existing valve from the patient's heart. One common technique employs a sewing ring or suture cuff which is attached to and extends around the outer circumference of the mechanical valve orifice. The sewing cuff is made of a biocompatible fabric suitable for allowing a needle and suture to pass therethrough. The sewing cuff is securely attached to the circumference of the mechanical valve orifice using sutures which are passed through the tissue annulus and the sewing cuff. The sutures are tied snugly, thereby securing the valve to the heart.

Sewing cuffs are expensive to manufacture and are difficult to secure to the valve orifice. It is also desirable to provide a large lumen through the valve orifice relative to the overall valve diameter. However, techniques for attaching the sewing cuff to the valve orifice typically require the area of the valve lumen be reduced to accommodate an attachment mechanism. For example, the sewing cuff is typically retained between two rims of the valve orifice. The lower rim normally defines the outside diameter of the valve orifice and thus limits the size of the valve lumen.

Another technique for attaching heart valves uses a series of pins which pierce the tissue annulus of the heart. The pins are crimped or bent, thereby locking the valve to the heart tissue and preventing the valve from separating from the heart. This technique is described in U.S. Pat. Nos. 3,574,865 and 3,546,710.

SUMMARY OF THE INVENTION

The present invention is a prosthetic heart valve for implantation in a heart. The heart valve includes an orifice body having an outer circumference and defining a lumen for blood flow therethrough. At least one leaflet occluder carried in the lumen of the orifice body is movable between an open position, which allows blood flow through the lumen, and a closed position which blocks blood flow through the lumen. A flange ring around the outer circumference of the orifice body includes a plurality of suture holes. The suture holes are adapted for receiving a suture and thereby attaching the heart valve to tissue of the heart.

In one embodiment, a suture receiving element around the outer circumference of the orifice body is axially spaced apart from the flange ring. The suture receiving element is adapted for receiving a suture passed through a suture hole in the flange ring and securing heart tissue between the flange ring and the suture receiving element.

DETAILED DESCRIPTION OF THE PREFERRED EMBODIMENTS

Figures 1A, 1B, 1C and 1D show exploded top perspective, top perspective, top plan and side plan views, respectively, of a mechanical heart valve in accordance with one embodiment of the present invention. The present invention provides a heart valve 10 having a suture flange for directly attaching to the tissue annulus of a heart. This provides a quick, convenient and easy method for attaching a prosthetic heart valve to the heart tissue annulus that remains after the native heart valve is removed by a surgeon. The technique also eliminates the need for a sculpted sewing ring or suture cuff used as a method of attaching the valve to the tissue annulus, thereby reducing the manufacturing costs of the valve.

Figure 1A:
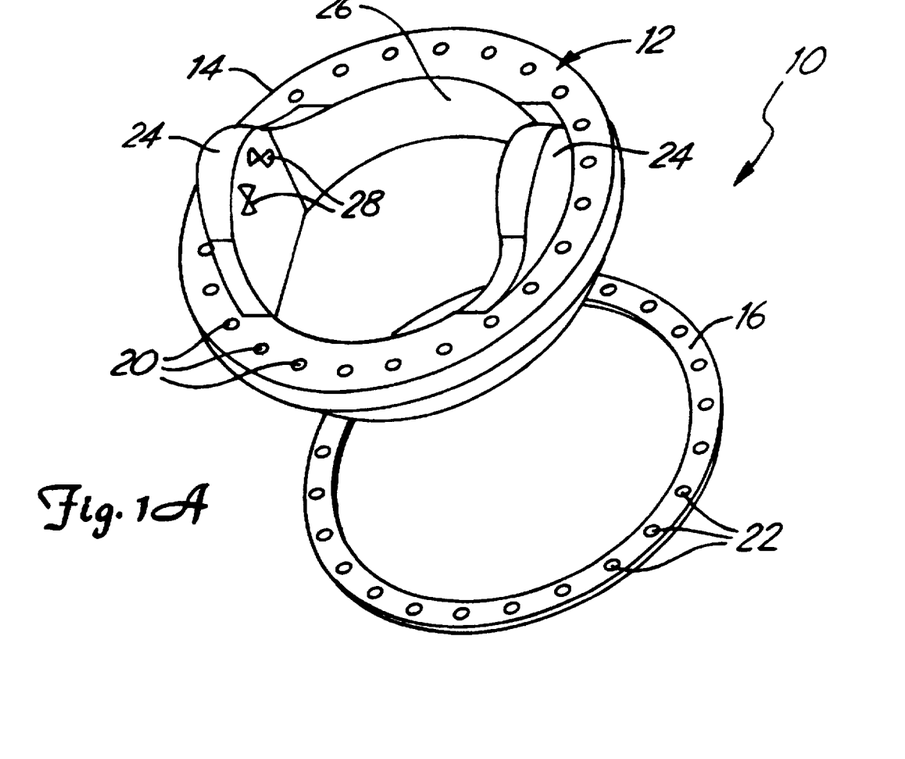
FIG. 1A is a top perspective exploded view of a mechanical heart valve in accordance with one embodiment.
Figure 1B:
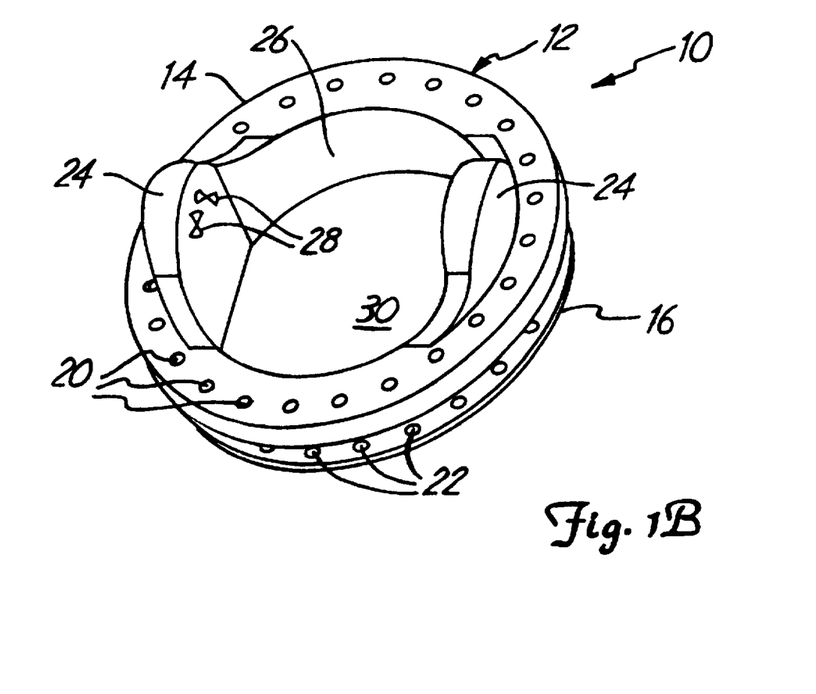
FIG. 1B is a top perspective view of the valve of FIG. 1A.
Figure 1C:
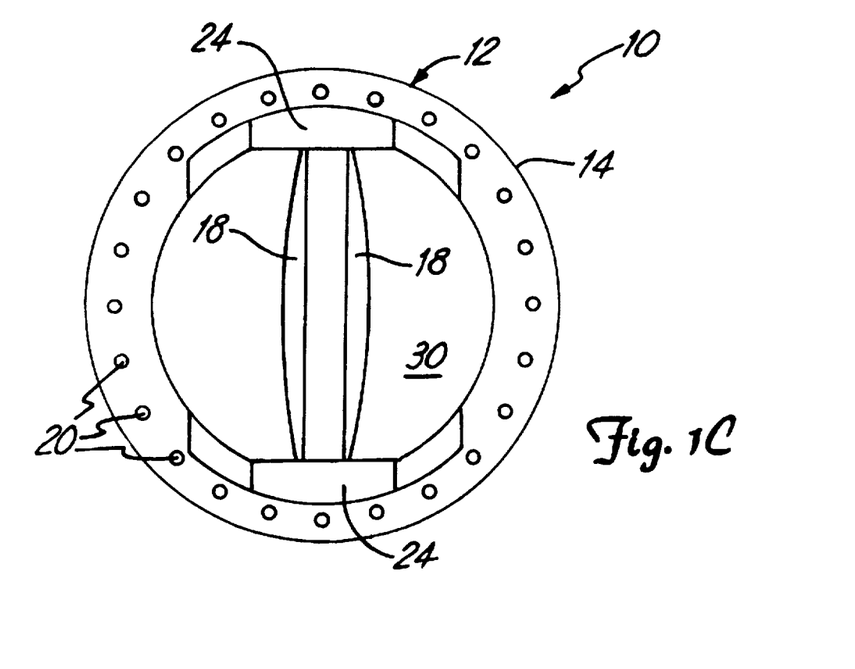
FIG. 1C is a top plan view of the valve of FIG. 1A.

Valve 10 includes orifice body 12, orifice flange (or flange ring) 14, flange ring 16 and leaflets 18 (shown in FIG. 1C). Orifice flange 14 is formed integral with orifice 12. Orifice flange 14 has a plurality of suture holes 20 formed therein. A cuff gasket 38 is positioned proximate orifice flange 14. Similarly, flange ring 16 includes suture holes 22. Orifice body 12 includes pivot guards 24 and central annulus 26 in which leaflets 18 and mated spherical pivots 28 are engaged. Leaflets 18 are movable about mated spherical pivots 28 between an open position which permits blood flow through lumen area 30, as in FIG. 1C, and a closed position which blocks blood flow through lumen area 30 defined in orifice body 12. Orifice flange ring 16 is separate from valve 10 and can be formed of a biocompatible metallic, polymeric or fabric material such as MP35N, Acctal or polyester, depending on the surgeon's needs and preferences.

Figure 1D:
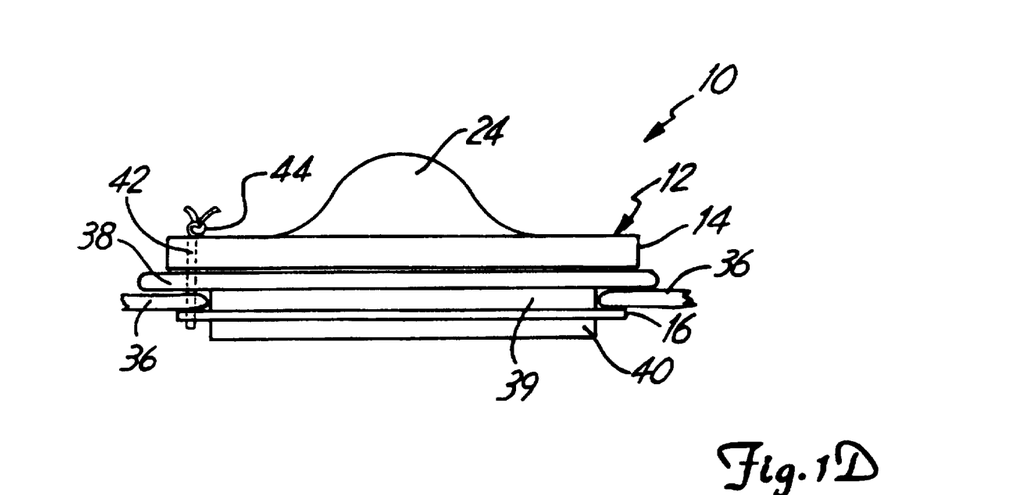
Figure 1D is a side plan view of the heart valve of FIG. 1A.

As shown in FIG. 1D, flange ring 16 is axially spaced apart from orifice flange 14 by tissue annulus 36 and cuff gasket 38. Also shown in FIG. 1D, an outer annulus region 40 is formed between flange ring 16 and the end of orifice 12 which allows for thickness variations in tissue annulus 36. Valve 10 is attached to tissue annulus 36 by passing a plurality of sutures 42 through suture holes 22 in flange ring 16, through tissue annulus 36, through cuff gasket 38, through holes 20 in orifice flange 14 of valve 10 and knotting sutures 42 securely with knots 44. Sutures 42 also secure flange ring 16 in position as shown in FIG. 1D, thereby clamping tissue annulus 36. Suture holes 20 and 22 are generally aligned to facilitate the passing of sutures 42. The total number of sutures 42 is determined by the surgeon. All holes 20,22 need not be used. The inner diameter of tissue annulus 36 fits snugly around the valve outer diameter 39 when valve 10 is inserted.

Figure 2A:
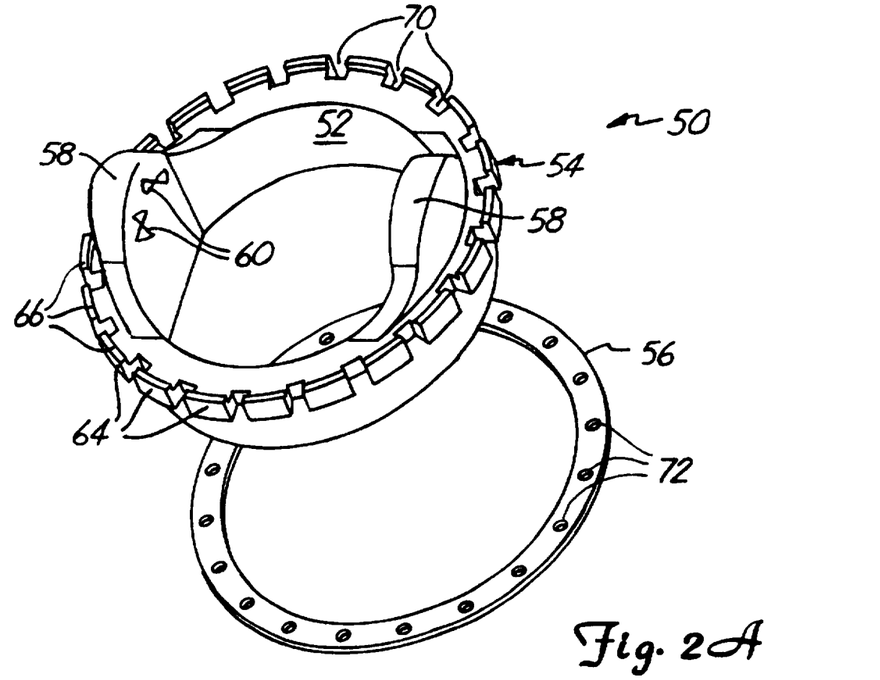
FIG. 2A is a top perspective exploded view of a mechanical heart valve in accordance with another embodiment.
Figure 2B:
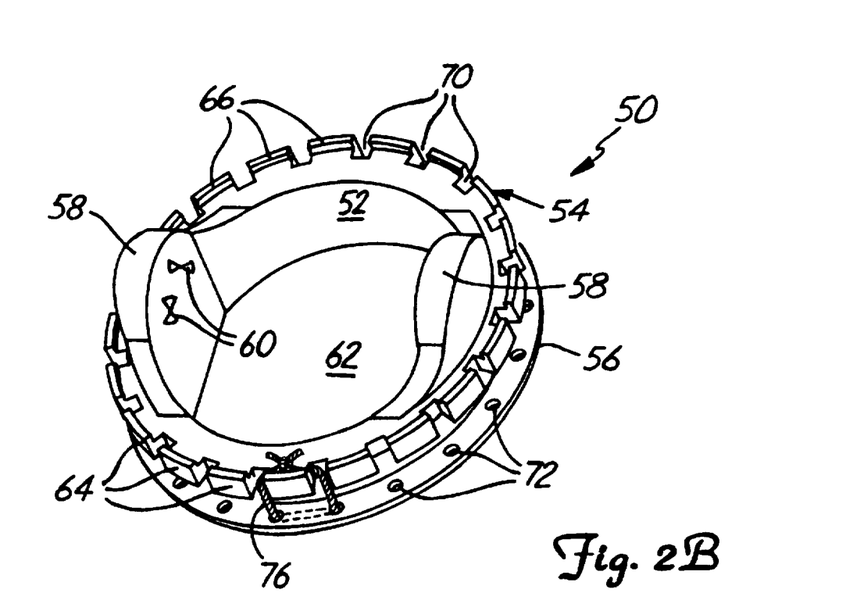
FIG. 2B is a top perspective view of the mechanical heart valve of FIG. 2A.
Figure 2C:
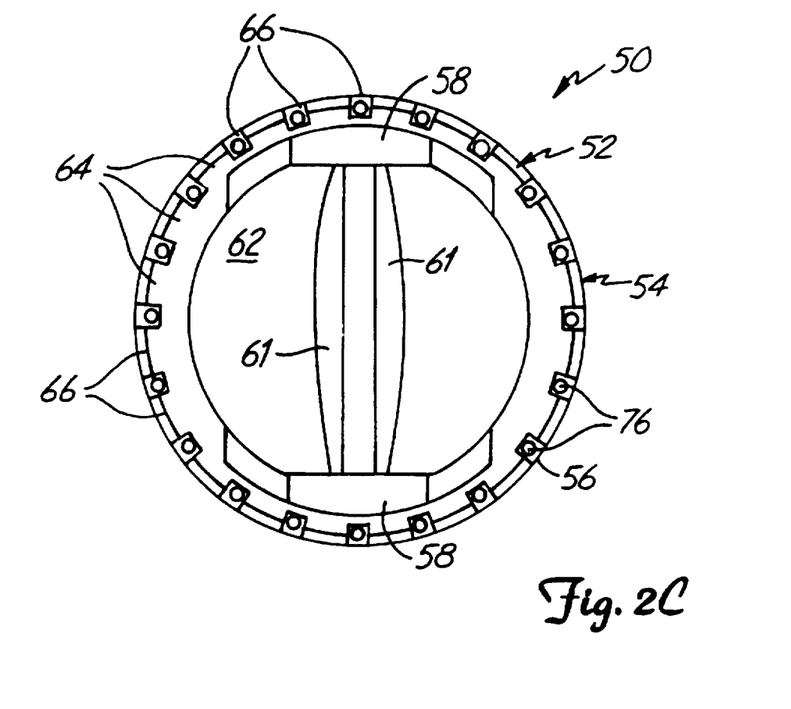
FIG. 2C is a top plan view of the mechanical heart valve of FIG. 2A.

FIGS. 2A, 2B, 2C and 2D show exploded top perspective, top perspective, top plan and side plan views, respectively, of mechanical heart valve 50 in accordance with another embodiment. Heart valve 50 includes orifice body 52 having integral orifice flange or flange ring 54 and flange ring 56. Orifice body 52 includes pivot guards 58 and mated spherical pivots 60, adapted for carrying leaflets 61 in lumen area 62. Orifice ring 54 is formed of a plurality of radial extensions 64 having suture retention lips 66. A cuff gasket 68 is positioned proximate orifice ring 54. Suture receiving notches 70 are formed between radial extensions 64. Flange ring 56 includes a plurality of suture holes 72 which are generally aligned with notches 70 as shown in FIG. 2C.

Figure 2D:
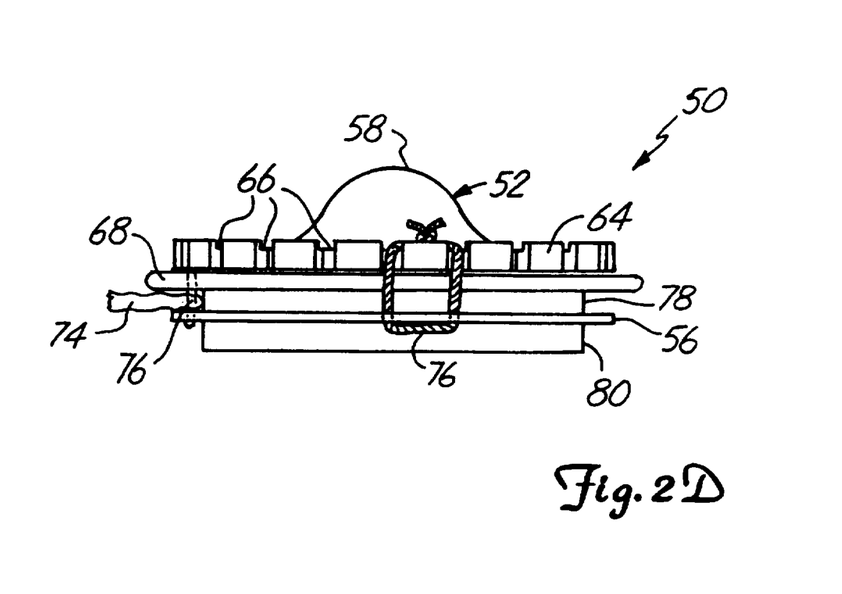
FIG. 2D is a side plan view of the mechanical heart valve of FIG. 2A.

Valve 50 is attached to a heart tissue annulus 74 using sutures 76, as shown in FIGS. 2B and 2D. Sutures 76 extend through suture holes 72, through tissue annulus 74, through cuff gasket 68, over a radial extension 64, through suture notches 70 and are knotted securely. Suture retention lips 66 prevent sutures 76 from sliding off extension 64. The inner diameter of tissue annulus 74 fits snugly around the valve outer diameter 78 when valve 50 is inserted. The position of flange ring 56 also forms an annulus extension 80 of orifice 52 which allows for variations in the tissue annulus thickness.

Figure 3A:
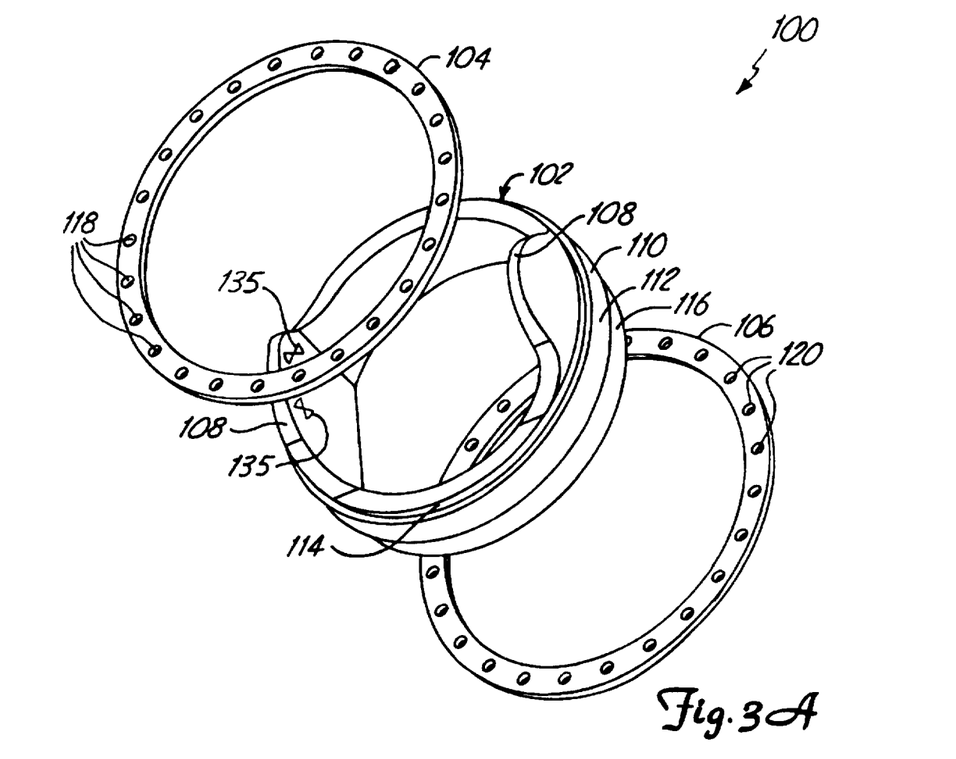
FIG. 3A is an exploded top perspective view of a mechanical heart valve in accordance with another embodiment.
Figure 3B:
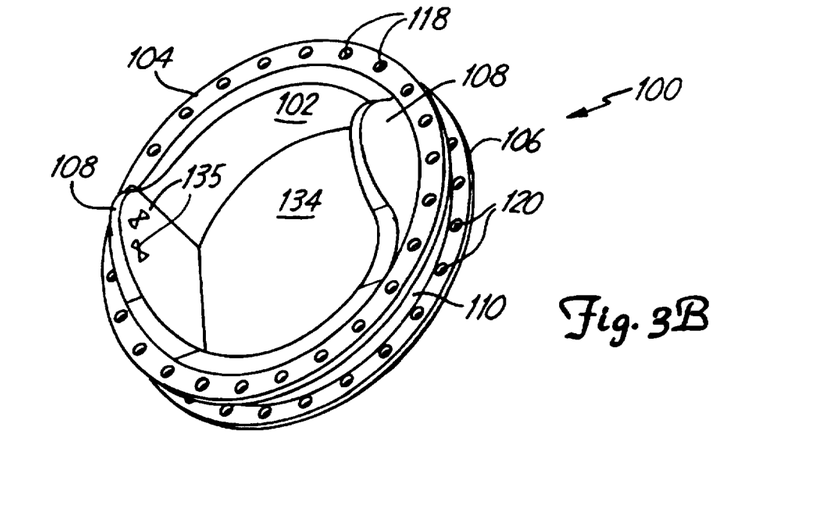
FIG. 3B is a top perspective view of the mechanical heart valve of FIG. 3A.
Figure 3C:
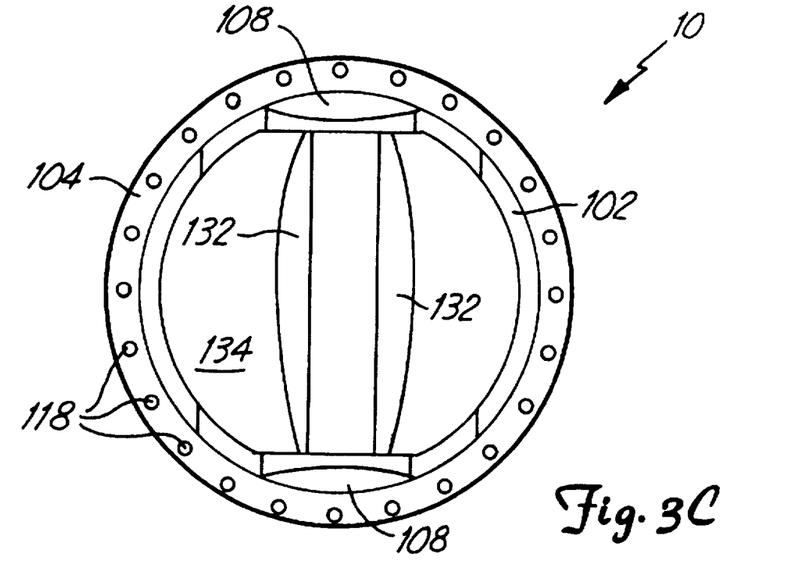
FIG. 3C is a top plan view of the mechanical heart valve of FIG. 3A.
Figure 3D:
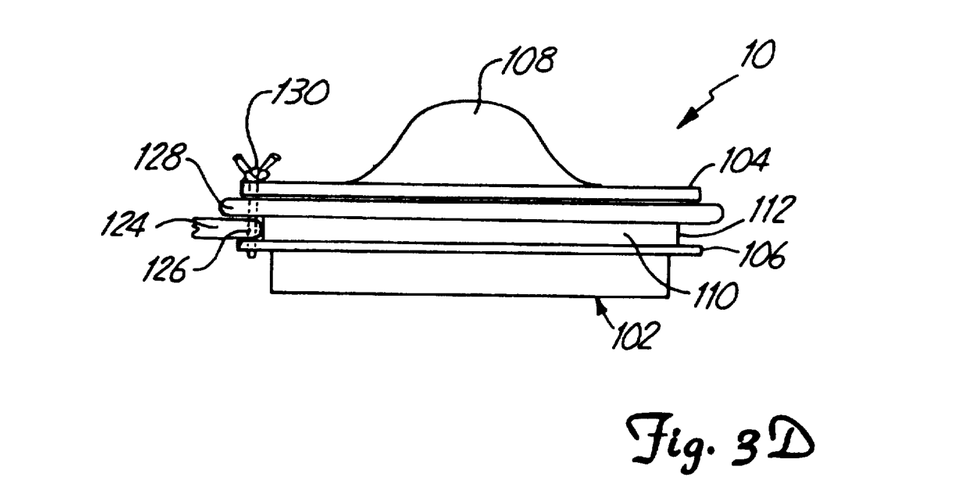
FIG. 3D is a side plan view of the mechanical heart valve of FIG. 3A.

FIGS. 3A, 3B, 3C and 3D show exploded top perspective, top perspective, top plan and side plan views, respectively, of mechanical heart valve 100 in accordance with another embodiment. As shown in FIG. 3A, valve 100 includes orifice body or housing 102 and flange rings (orifice flanges) 104 and 106. Orifice body 102 includes pivot guards 108 and rim 110 which is formed integral with orifice body 102 and extends around the outer circumference of orifice body 102. Upper orifice outer diameter 114 and lower orifice outer diameter 116 are sized to match the inner diameter of their respective flange rings 104 and 106. Flange ring 104 includes a plurality of suture holes or openings 118, and flange ring 106 includes a plurality of suture holes or openings 120. FIGS. 3B and 3D show valve 100 with flange rings 104 and 106 abutted against rim 110. Suture holes 118 are substantially aligned with suture holes 120 as shown in FIG. 3D. Attachment to heart tissue annulus 124 is accomplished by passing a suture 126 through holes 120 on lower flange ring 106, through tissue annulus 124, through cuff gasket 128, through holes 118 on upper flange ring 104 and securely knotting sutures 126 together with suture knot 130.

FIG. 3C is a top plan view of valve 100. Occluder leaflets 132 are shown in lumen area 134 and are movable in mated spherical pivots 135. FIG. 3D is a side plan view of valve 100 showing valve 100 attached to heart tissue annulus 124. Tissue annulus 124 and cuff gasket 128 fit between flange rings 104 and 106, as shown in cross section in FIG. 3D. Cuff gasket 128 conforms to irregular tissue geometry that may result from removal of the existing valve, valve calcification or other causes, and as a gasket to reduce perivalvular leakage. Tissue annulus 124 engages the valve outer diameter 112 snugly when valve 100 is inserted to create a seal and reduce blood leakage. Sutures 126 secure valve 100 to tissue annulus 124. In one embodiment, these same sutures 126 are used to maintain flange rings 104 and 106 in abutting contact with rim 110.

FIGS. 1A through 3D are shown wit-h a lower flange ring. Alternatively, it is within the contemplation of the invention to not provide the lower flange ring.

FIGS. 1 through 5 illustrate mitral heart valve embodiments. The embodiments are equally applicable to other heart valves.

In the designs shown in FIGS. 1A through 3C, it is desirable to reduce and prevent perivalvular leakage. This may be achieved by including a biocompatible gasket made from a soft, compliant material which lies in contact with and between the tissue annulus and the upper or lower flange rings. This thin layer of material acts as a pad to conform to irregular tissue contours which result from removal of the existing valve, heart disease and calcification and is intended to minimize perivalvular leakage. This component of the design is described below in greater detail.

Figure 4:
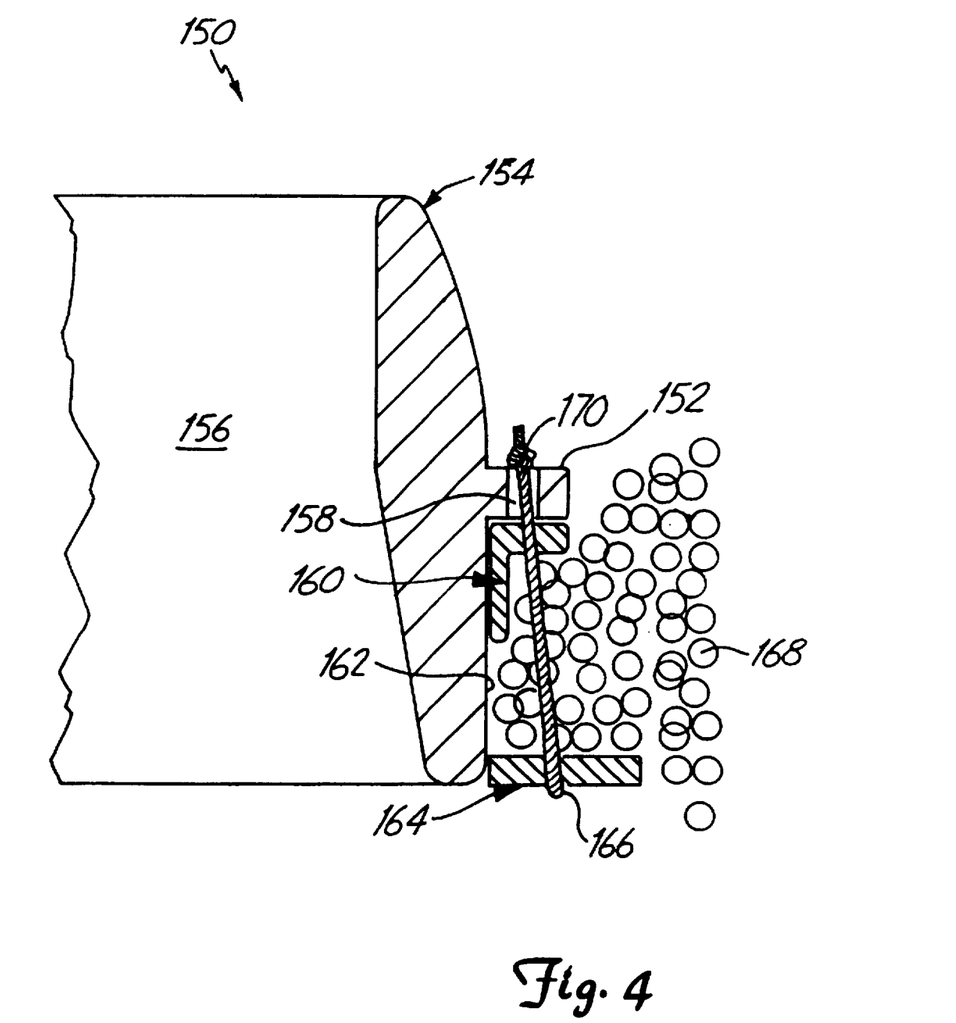
FIG. 4 is a cross-sectional view of a mechanical heart valve in accordance with another embodiment.

FIG. 4 is a cross-sectional view of a mechanical heart valve 150 having a single orifice flange or flange ring 152 in accordance with another embodiment. Valve 150 includes orifice body 154 defining a lumen 156 therethrough. Orifice flange 152 is formed integral with orifice body 154 and includes suture hole 158 extending therethrough. A biocompatible fabric flange gasket 160, such as polyester, extends around valve annulus 162, as shown in FIG. 4. Flange ring 164 extends around annulus 162 and provides a suture receiving element similar to the flange rings of valves 10, 50, and 100 described above. A suture 1)6 extends through suture hole 158 of orifice flange 152, heart tissue annulus 168 and flange ring 164, and thereby attaches valve 150 to heart tissue annulus 168. A suture knot 170 secures suture 166 to orifice flange 152. Fabric ring 160 acts as a gasket to prevent and reduce perivalvular leakage. Further, flange ring 164 prevents suture 166 from being drawn through or into heart tissue annulus 168. In embodiments where flange ring 164 is made rigid (see valves 10, 50 and 100 discussed above), the suture 166 can be drawn tight thereby compressing heart tissue annulus 168 to further reduce the likelihood of perivalvular leakage.

Figure 5:
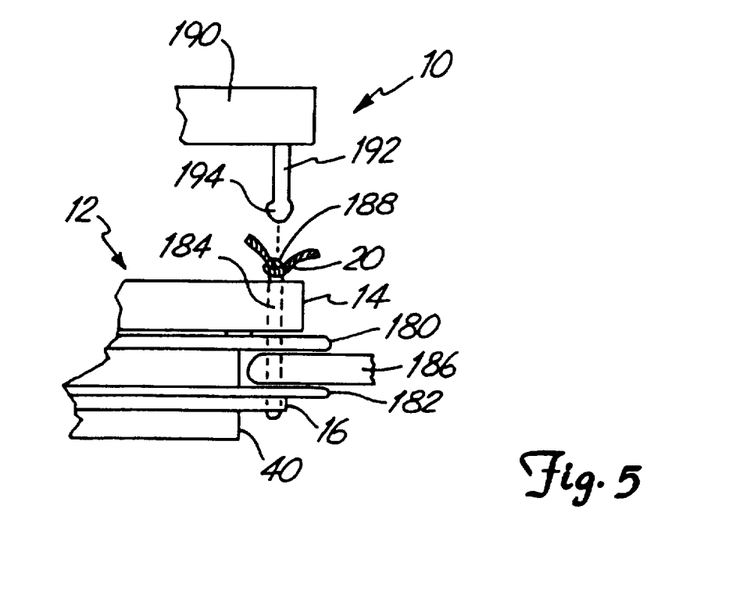
FIG. 5 is a cross-sectional view showing a mechanical heart valve attached to the heart tissue annulus in accordance with one technique of the present invention.

Attachment to heart tissue of the valves described herein may be through any suitable means. A number of techniques will be described in greater detail. FIG. 5 is a cross-sectional view of valve 10 shown in FIGS. 1A through 1D which includes gaskets 180 and 182 to reduce perivalvular leakage. As shown in FIG. 5, a gasket 180 is provided adjacent orifice flange (or flange ring) 14. Similarly, gasket 182 is adjacent flange ring 16. A suture 184 extends through flange ring 16, gasket 182, heart tissue annulus 186, gasket 180 and suture hole 20 in orifice flange 14. A suture knot 188 secures suture 184 to valve 10. Gaskets 180 and 182 help seal the annulus of valve 10 to heart tissue annulus 186. Gaskets 180 and 182 will tend to conform to irregular heart tissue, for example calcified tissue irregularities. Gaskets 180 and 182 can be supplied to a surgeon in a variety of shape, size and thickness configurations so an appropriate gasket may thus be chosen for each individual procedure. FIG. 5 also shows orifice cap 190 having a plurality of plugs 192. In one embodiment, cap 190 is ring-shaped having a plurality of plugs 192 aligned with suture holes 20. Plugs 192 are inserted into suture holes 20 and locked in place by enlarged tip 194. Plug 192 helps secure suture 184 in hole 20 thereby preventing suture 184 from being pulled back through hole 20.

Figure 6:
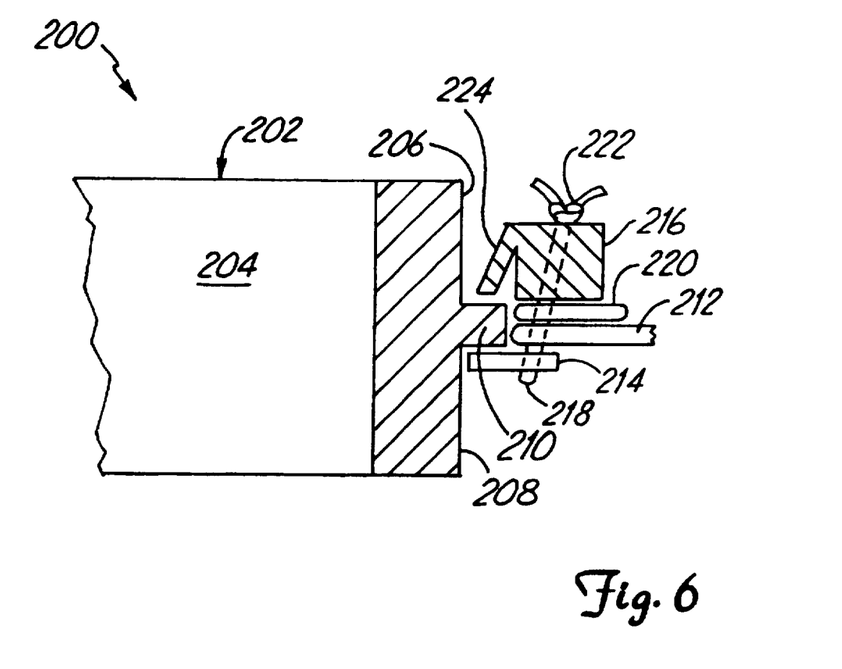
FIG. 6 is a cross-sectional view depicting a technique for attaching a mechanical heart valve to a heart tissue annulus in accordance with another embodiment.

FIG. 6 is a cross-sectional view showing heart valve 200. Valve 200 includes orifice 202 forming lumen 204 therethrough. Orifice 202 provides annulus 206 and annulus 208 separated by rim 210. Valve 200 is attached to heart tissue annulus 212 using flange ring 214 and flange ring 216. A suture 218 extends through flange ring 214, heart tissue annulus 212, gasket material 220 and flange ring 216, and is secured to flange ring 216 with suture knot 222. Flange ring 216 includes cantilevered spring 224 which abuts rim 210. Cantilevered spring 224 allows valve 200 to be implanted as a two-piece valve. After suturing flange rings 214 and 216 to the heart tissue annulus 212, orifice 202 can be snapped into place and locked between cantilevered spring 224 and flange ring 214. This may ease the implantation of small valves by allowing increased visibility of the operating field during suturing. Additionally, this configuration allows easy viewing and access of the ventricular side of the heart tissue annulus 212 prior to insertion of orifice 202.

Figure 7:
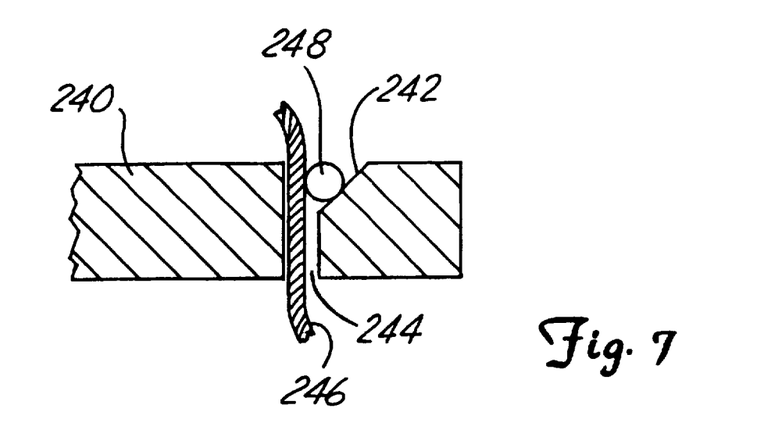
FIG. 7 is a cross-sectional view showing a technique for attaching a suture to a flange ring in accordance with one embodiment.

FIG. 7 shows a cross-sectional view of flange ring 240 having chamfered slot 242 and suture hole 244. Flange ring 240 is adapted for securing a suture 246 without requiring a suture knot. A ball or cylinder 248 fits in chamfered slot 242. As suture 246 is pulled through opening 244, ball 248 is pulled deeper into chamfered slot 242 thereby squeezing suture 246 against flange 240. However, if suture 246 is pulled in the opposite direction, suture 246 meets with no resistance from ball 248.

Figure 8:
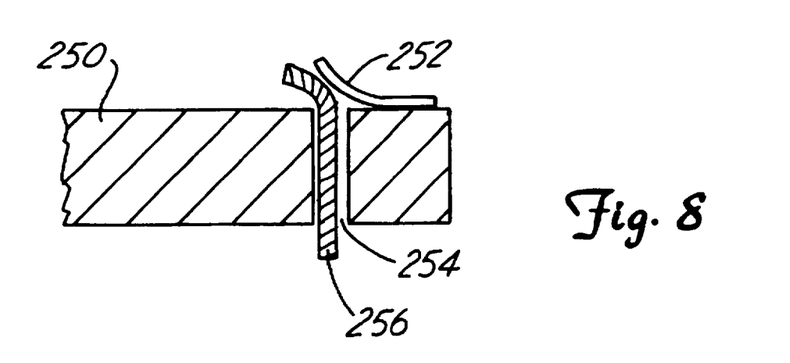
FIG. 8 is a cross-sectional view of a flange ring showing a technique for attaching a suture to a flange ring in accordance with another embodiment.

FIG. 8 is a cross-sectional view of flange 250 including spring 252 over suture opening 254. Spring 252 presses against suture 256 thereby locking suture 256 to flange 250. These embodiments provide reduced implantation time because a surgeon is not required to knot the sutures. These techniques are well suited for use with the stiff orifice flanges and flange rings described herein.

A mechanical valve set forth herein in a typical implantation will have a portion which sits subannular, a portion which fits intra-annular and a portion which resides supra-annular relative to the heart tissue annulus. In general, the heart tissue annulus fits between the two flanges, and the valve extends both subannularly and supra-annularly. The embodiments set forth herein eliminate the sewing ring or suture cuff currently used, the manufacture of which is labor intensive. The sewing cuff can be replaced by a separate gasket which can be easily mass produced, reducing manufacturing cost and offering the surgeon a broader range of gasket styles to match individual case scenarios. Further, the gaskets set forth reduce perivalvular leakage. Additionally, the flanges can be adapted for use with suture attachment techniques which do not require a suture knot. Further, the embodiments may allow enlarging the lumen area thus offering less restriction to blood flow through the orifice.

Although the present invention has been described with reference to preferred embodiments, workers skilled in the art will recognize that changes may be made in form and detail without departing from the spirit and scope of the invention.

What is claimed is:

1. A prosthetic heart valve for implantation in a heart, comprising:

an orifice body having an outer circumference and defining a lumen therethrough;

at least one occluder carried in the lumen of the orifice body and movable between an open position allowing flow through the lumen and a closed position blocking flow therethrough;

an orifice flange having a plurality of suture holes defined therein, the orifice flange extending around and generally conforming to the outer circumference of the orifice body, the plurality of suture holes adapted for receiving a suture therethrough;

a separate flange ring shaped to generally conform to the outer circumference of the orifice body and having a plurality of suture holes defined therein adapted for receiving the suture for attaching the heart valve to tissue of the heart and urging the orifice flange and the flange ring together such that a tissue annulus of the heart can be securely held between the orifice flange and the flange ring to reduce blood leakage therepast; and a gasket adjacent one of either the orifice flange or the flange ring for forming a tissue seal between the one flange ring and the tissue annulus to reduce blood leakage.

2. The prosthetic heart valve of claim 1 wherein the orifice flange is integral with the orifice body.

3. The prosthetic heart valve of claim 1 wherein the suture holes of the orifice flange comprise a plurality of suture receiving notches defined therein.

4. The prosthetic heart valve of claim 3 wherein the orifice flange includes a plurality of suture retaining lips adjacent the plurality of notches.

5. The prosthetic heart valve of claim 1 wherein the flange ring includes a suture locking mechanism.

6. The prosthetic heart valve prosthesis of claim 1 including a second gasket adjacent the orifice flange for forming a tissue seal between the orifice flange and the tissue annulus to reduce blood leakage.

7. The prosthetic heart valve of claim 5 wherein the suture locking mechanism comprises a cap having a plug adapted to fit into a suture hole thereby locking the suture in place.

8. The prosthetic heart valve of claim 5 wherein the suture locking mechanism comprises a chamfered slot formed in a suture hole and ball fitting therein to secure the suture between the ball and the chamfered slot.

9. The prosthetic heart valve of claim 5 wherein the suture locking mechanism comprises a spring adjacent a suture hole positioned to apply pressure to the suture.

10. A prosthetic heart valve for implantation in a heart, comprising:

an orifice body having an outer circumference and defining a lumen therethrough, the orifice body including a rim;

at least one occluder carried in the lumen of the orifice body and movable between an open position allowing flow through the lumen and a closed position blocking flow therethrough;

a first flange ring having a plurality of suture holes defined therein, the first flange ring extending around and generally conforming to the outer circumference of the orifice body, the plurality of suture holes adapted for receiving a suture therethrough; and a second flange ring shaped to generally conform to the outer circumference of the orifice body and having a plurality of suture holes defined therein adapted for receiving the suture for attaching the heart valve to tissue of the heart and urging the first ring and the second flange ring together such that a tissue annulus of the heart can be securely held between the first flange ring and the second flange ring to reduce blood leakage therepast;

wherein the rim separates the first flange ring and the second flange ring such that at least one of the flange rings abuts the rim.

11. The prosthetic heart valve of claim 10 wherein the suture holes of the first ring comprise a plurality of suture receiving notches defined therein.

12. The prosthetic heart valve of claim 11 wherein the first ring includes a plurality of suture retaining lips adjacent the plurality of notches.

13. The prosthetic heart valve of claim 10 including a gasket adjacent the flange ring for forming a tissue seal between the second flange ring and the tissue annulus to reduce blood leakage.

14. The prosthetic heart valve prosthesis of claim 13 including a second gasket adjacent the first ring for forming a tissue seal between the first ring and the tissue annulus to reduce blood leakage.

15. The prosthetic heart valve of claim 10 wherein the second flange ring includes a suture locking mechanism adjacent the suture hole for locking a suture therein.

16. The prosthetic heart valve of claim 15 wherein the suture locking mechanism comprises a cap having a plug adapted to fit into a suture hole thereby locking the suture in place.

17. The prosthetic heart valve of claim 15 wherein the suture locking mechanism comprises a chamfered slot formed in a suture hole and ball fitting therein to secure the suture between the ball and the chamfered slot.

18. The prosthetic heart valve of claim 15 wherein the suture locking mechanism comprises a spring adjacent a suture hole positioned to apply pressure to the suture.

* * * * *

UNITED STATES PATENT AND TRADEMARK OFFICE
CERTIFICATE OF CORRECTION

PATENT NO. : 5,776,188
DATED : July 7, 1998
INVENTOR(S) : Terry L. Shepherd et al.

It is certified that error appears in the above-indentified patent and that said Letters Patent is hereby corrected as shown below:

Col. 6, line 32, after "mechanism" insert --adjacent the suture hole for locking a suture therein--.

Signed and Sealed this

Second Day of February, 1999

Attest:

Attesting Officer

*Acting Commissioner of Patents and Trademarks*